United States Patent [19]  [11]  4,395,406
Gacek et al.  [45]  Jul. 26, 1983

[54] 5-HALOPYRIMID-2-ONES

[75] Inventors: Mikkel J. Gacek; Reidar Oftebro; Soren Laland; Kjell Undheim, all of Oslo, Norway

[73] Assignee: Nyegaard & Co. A/S, Norway

[21] Appl. No.: 166,600

[22] Filed: Jul. 7, 1980

Related U.S. Application Data

[63] Continuation of Ser. No. 61,269, Jul. 27, 1979, abandoned, which is a continuation of Ser. No. 937,579, Aug. 29, 1978, abandoned, which is a continuation of Ser. No. 732,189, Oct. 13, 1976, abandoned.

[30] Foreign Application Priority Data

Oct. 16, 1975 [GB] United Kingdom ............... 42509/75

[51] Int. Cl.³ .................. A61K 31/505; C07D 239/36; C07D 239/56
[52] U.S. Cl. ..................................... 424/180; 424/251; 536/23; 544/303; 544/311; 544/313; 544/315; 544/316; 544/318
[58] Field of Search ............... 544/315, 303, 309, 311, 544/313, 316, 318; 424/251, 180

[56] References Cited

U.S. PATENT DOCUMENTS

3,317,532  5/1967  Gamaliel et al. .................... 544/315
3,833,586  9/1974  Schwan et al. ...................... 544/315
4,003,900  1/1977  Schwan ............................... 544/315
4,014,996  3/1977  Maurer et al. ...................... 544/315

OTHER PUBLICATIONS

Stark, Annellen der Chemie, 381, pp. 143–155, (1911).
Ueda et al., J. Med. Chem., vol. 6, pp. 697–701.
Brown et al., Aust. J. Chem., 1968, vol. 21, pp. 243–255.

*Primary Examiner*—Paul M. Coughlan, Jr.
*Attorney, Agent, or Firm*—Bacon & Thomas

[57] ABSTRACT

Novel derivatives of pyrimid-2-one having interesting pharmacological properties are described. The compounds of the invention have been found to be of use in the control of, and in particular in the inhibition of the metaphase of malignant tumours and leukaemias. Processes for the preparation of the novel compounds and pharmaceutical compositions containing them are also described.

9 Claims, No Drawings

5-HALOPYRIMID-2-ONES

This is a continuation of application Ser. No. 61,269, filed July 27, 1979, which is in turn a continuation of Ser. No. 937,579, filed Aug. 29, 1978, which is in turn a continuation of Ser. No. 732,189, filed Oct. 13, 1976, all now abandoned.

This invention relates to compounds which are of use in the control of malignant tumours and leukaemias.

Cell growth and division in malignant tumours and leukaemias generally follows the same sequence as the growth of normal cells. This growth cycle can be divided into a number of individual phases, of which one is the metaphase.

The present invention is concerned with inhibition of the metaphase in the growth of malignant tumours and leukaemias.

In the chemotherapy of malignant tumours and leukaemias, one method of preventing metastatic growth and arresting the rapid multiplication of malignant cells has been to arrest complete growth by hindering or preventing the development of the cell in the metaphase. Agents which are suitable for this type of therapy have been termed metaphase inhibitors, and they may be used either alone or, more usually, in combination with other anti-cancer agents. Since the metaphase inhibitor has the effect of holding the tumour cells in the mitotic phase and in many instances bringing them into synchronous growth, tumour cells treated with a metaphase inhibitor are more susceptible to attack by certain chemotherapeutics, notably bleomycin and Ara-C.

One such inhibitor which we have recently developed is 5-fluoro-pyrimid-2-one. (Biochem. Pharm. 21.2451–2456).

This compound was unexpectedly found to have a metaphase growth inhibiting effect in studies which attempted to explain why the compound itself did not inhibit DNA synthesis while its desoxyribosyl derivative did. The compound has now been found not to be incorporated into DNA and RNA. Its 5-chloroanalogue has also been described.

We have now prepared a wide range of pyrimid-2-one derivatives that are of interest as metaphase inhibitors.

According to one aspect of this invention, therefore, we provide compounds of the formula

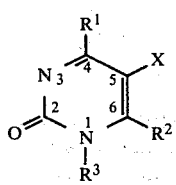

wherein
X represents a fluorine, chlorine or bromine atom;
$R^1$ and $R^2$, which may be the same or different, each represent hydrogen or a group Alk or SAlk; and
$R^3$ represents hydrogen or a group Alk or a glycosyl group other than a 1-ribofuranosyl or 1-desoxyribofuranosyl group, Alk being an alkyl, alkenyl or alkynyl group having up to 4 carbon atoms, which group may carry one or more halogen atoms or oxo groups or optionally substituted phenyl, hydroxyl, mercapto, carboxyl, carboxamido or amino groups at least one of the groups $R^1$, $R^2$ and $R^3$ being other than hydrogen, $R^1$ or $R^2$ only being an unsubstituted saturated S-alkyl group when $R^3$ is a group Alk and salts thereof.

Previously, the principal metaphase inhibitors proposed for use in treatment of cancer have been the alkaloids vincristine and vinblastine. However, these substances are toxic and their use has consequently proved hazardous. They appear to produce an adverse effect on nerve cells and on protein transport.

In contrast, the compounds of the invention are markedly non-toxic, in this respect being generally superior to the unsubstituted parent compounds in which $R^1$, $R^2$ and $R^3$ are all hydrogen. While we do not wish to be limited by theoretical considerations, it is believed that the unsubstituted 5-halo-pyrimid-2-ones are oxidised in the liver to the corresponding 5-halo-uracils which are markedly toxic, although beneficial anti-cancer agents when administered correctly. Such toxicity arises in part from incorporation of the 5-halo uracil into DNA and we believe that in the compounds of the present invention both the oxidation to uracils and the incorporation of the latter into DNA are inhibited by substitution. It is noteworthy, however, that we have tested many possible substituted 5-halo-pyrimidines which prove to be inactive as metaphase inhibitors so that the nature and position of the possible substituents is clearly significant.

$R^1$, $R^2$ and $R^3$, which may be the same or different, advantageously represent hydrogen or a methyl group, which may advantageously carry a phenyl or esterified carboxyl group, or an alkyl or propargyl group which may carry a terminal chlorine atom; it is generally preferred that only one of $R^1$ and $R^2$ is other than hydrogen.

In compounds wherein Alk— carries a substituted hydroxyl, —SH, carboxyl, carboxamido or amino group, the substituent (or, in the case of amino groups, substituents) on said group may for example be a lower alkyl, alkenyl or alkynyl group, preferably with 1–4 carbon atoms or a sugar. Preferred esterified carboxyl groups are ethoxycarbonyl groups. Sugar residues will preferably be present as substituents of hydroxyl or amino groups in Alk—. It will be appreciated that with some Alk groupings the active compounds will exist in geometrically or optically isomeric forms and that the invention extends to all of these.

Glycosyl groups present in the 1-position include 5- and 6-carbon sugar derivatives, in particular glucofuranone derivatives. Such glycosyl groups are linked to the nitrogen atom at the 1-position of the glycosyl ring. The hydroxyl groups of the glycosyl group may, if desired, be protected e.g. by acylation for example as acetoxy group or by acetonide formation, or may be replaced by an amino group which itself may be protected e.g. by acylation for example as an acetamido group. As indicated above, ribofuranosyl and desoxyribofuranosyl groups linked through the 1-position in the sugars are excluded; this is because such groups would permit the compound, after oxidation to a uracil derivative, to be incorporated into RNA or DNA with consequent toxic effects.

Particularly preferred compounds of the invention, in approximate order of antimitotic effectiveness are:
1. 1-Propargyl-5-bromopyrimid-2-one
2. 1-Propargyl-5-chloropyrimid-2-one
3. 1-(3-Chloroallyl)-5-bromopyrimid-2-one
4. 1-Propargyl-5-fluoropyrimid-2-one
5. 1-(3-Chloroallyl)-5-chloropyrimid-2-one 6. 1-Propargyl-4-propargylthio-5-fluoropyrimid-2-one
7. 1-Allyl-5-chloropyrimid-2-one
8. 1-Allyl-5-bromopyrimid-2-one
9. 1-Benzyl-5-fluoropyrimid-2-one
10. 1-(2-Chloroethyl)-5-bromopyrimid-2-one
11. 1-(2-Chloroethyl)-5-chloropyrimid-2-one
12. 1-Propargyl-4-methylthio-5-fluoropyrimid-2-one
13. 4,6-Dimethyl-5-bromopyrimid-2-one
14. Ethyl ester of 1-carboxymethyl-5-chloropyrimid-2-one
15. Ethyl ester of 1-carboxymethyl-5-fluoropyrimid-2-one
16. 1-Allyl-5-fluoropyrimid-2-one
17. 4-Allylthio-5-fluoropyrimid-2-one
18. 1,4-Dimethyl-5-bromopyrimid-2-one
19. 1-(2-Desoxy-2-acetylamino-D-glucopyranosyl)-5-chloropyrimid-2-one
20. 1-(2-Hydroxyethyl)-5-chloropyrimid-2-one
21. 1-(2-Hydroxyethyl)-5-fluoropyrimid-2-one
22. 1-(2-Hydroxy-3-chloropropyl)-5-bromopyrimid-2-one
23. 1-(2-Hydroxy-3-chloropropyl)-5-chloropyrimid-2-one
24. 1-Propyl-5-fluoropyrimid-2-one
25. 1-(2-Hydroxyethyl)-5-bromopyrimid-2-one
26. 1-(2,3-Dihydroxypropyl)-5-chloropyrimid-2-one
27. 1-(2-Hydroxy-3,3,3-trichloropropyl)-5-bromopyrimid-2-one
28. 1-(2-Dimethylaminoethyl)-5-chloropyrimid-2-one
29. 1-Carboxymethyl-5-fluoropyrimid-2-one
30. 4-Methylthio-5-bromo-6-methylpyrimid-2-one
31. 4-Methylthio-5-chloropyrimid-2-one
32. 4-Methylthio-5-bromopyrimid-2-one Salts of compounds of formula I may include salts with alkali metal or alkaline earth metals e.g. sodium, potassium, magnesium or calcium, or ammonium (including substituted ammonium) salts. Compounds according to the invention carrying hydroxyl or amino groups also in general, possess enhanced water-solubility, the latter, of course, forming acid addition salts e.g. with mineral acids such as hydrochloric or sulphuric acid or organic acids such as acetic, tartaric or citric acid. However, in general, non-ionic compounds of the invention are preferred.

The compounds of the invention are structurally quite simple and may be prepared by a variety of different processes. Reactions for the preparations of the six-membered pyrimidine ring system from urea and three carbon atom components are well known in the art.

According to another aspect of the invention, therefore, we provide a process for the preparation of a compound of formula I as defined above wherein:

(a) A compound of formula II

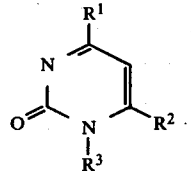

(II)

wherein $R^1$, $R^2$ and $R^3$ are as defined above, is allowed to react either with an electrophilic halogenating agent, for example molecular halogen, e.g. chlorine or bromine or a perfluoroalkylhypofluorite, or an N-halo imide or amide e.g. of a mono-or di-carboxylic acid having 2–6 carbon atoms, for example N-bromo-succinimide or N-chloroacetamide. Such direct nuclear halogenation reactions are desirably effected at around ambient temperature in a suitable solvent. Water is a convenient solvent for the direct halogenation reaction with molecular halogen and a polar, non-aqueous solvent e.g. acetic acid/acetic anhydride is suitable for the N-haloimide reaction. It is preferred that when $R^1$ is other than a hydrogen atom, and an N-haloimide reagent is used, the reagent of choice is N-bromosuccinimide.

(b) A compound of formula I, wherein $R^3$ is a hydrogen atom, or an alkali metal salt thereof is allowed to react with an alkylating agent serving to introduce the group Alk. This may, for example, be a compound of formula Alk, Y, wherein Alk is as defined above and Y is a halogen atom or a reactive ester derivative, optionally, but preferably, at an alkaline pH in the absence of water. Depending on whether or not a salt of the pyrimid-2-one is used, the presence of a base, e.g. an alkali metal hydroxide, e.g. potassium hydroxide, may be advantageous as an acid binding agent. Y a halogen, e.g. chlorine bromine or iodine, atom or reactive ester derivative e.g. a hydrocarbon sulphonyloxy derivative such as a mesylate, brosylate or tosylate. This method is particularly suitable when $R^3$ represents an alkyl, alkenyl or alkynyl group, optionally substituted by one or more hydroxy groups or carboxy groups, or substituted derivatives thereof.

Alternatively, the alkylating agent may be an unsaturated aliphatic compound wherein the unsaturated aliphatic grouping reacts with the ring nitrogen. Such as a reagent may be an olefin or acetylene which may carry substituents. Where such substituents are displacable, e.g. halogen atoms, the position which reacts with the nitrogen will depend on the reactivity of the unsaturated bond. In general, it is preferred that the unsaturated bond should be activated e.g. by an adjacent carbonyl group as, for example, in methylethynylketone.

(c) An intermediate having the formula I wherein $R^1$ represents —SH or its tautomeric thione of formula (III)

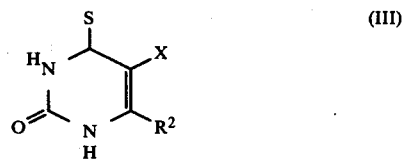

(III)

is converted into a compound of formula I wherein $R^1$ is —SAlk by treatment thereof with a compound AlkY as defined in (b) above at an alkaline pH. Alk— is preferably an alkyl group, optionally substituted by a carboxyl or substituted carboxyl group, and Y is preferably a halogen atom, e.g. a chlorine, bromine or iodine atom. The alkaline pH may be achieved either by employing an alkali metal, e.g. sodium or potassium, salt of the compound of formula I used as starting material, or by carrying the reaction out in the presence of base, e.g. an alkali metal hydroxide, for example, sodium or potassium hydroxide. Where it is desired to produce a thioalkyl group substituted by a carboxyl group, it has been found convenient to use a compound AlkY carrying an esterified carboxyl group to prepare an ester derivative followed by a conventional deesterification reaction, e.g. basic hydrolysis; where a base is used in the reaction, a carboxyl group will usually be formed in situ.

The intermediate in which $R^1$ is —SH or its tautomeric thione may be prepared by reacting a compound of the formula V

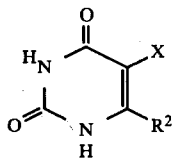

wherein $R^2$ and X are as defined above with a reagent serving to convert the 4-oxo group into a $>C=S$ group. A convenient reagent for this purpose is phosphorus pentasulphide.

(d) A thione compound of the formula III as defined above is desulphurised by use of a reductive metal catalyst, preferably Raney nickel. The reaction is preferably effected in a basic solvent, e.g. aqueous ammonia and the reaction mixture heated. The product of formula I has the formula

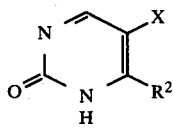

which is identical with the compound

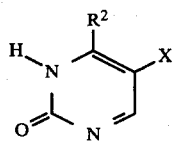

in view of the equivalence of the 4- and 6-positions. Similarly a compound of formula I in which $R^1$ is a group —SAlk may also be desulphurised by such reagents.

(e) replacement of the $NH_2$ group of a compound of the formula

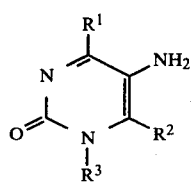

(where $R^1$, $R^2$ and $R^3$ have the above meanings) by a halogen atom by diazotisation of said amino group and reaction of the diazonium salt so formed with a cuprous halide, with a hydrohalic acid in the presence of copper powder or with fluoroboric acid followed by decomposition of the initial borofluoride.

(f) Hydrolysis to effect replacement of the group Y by OH in a compound of the formula

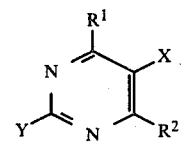

or a derivative thereof wherein one nitrogen carries a group Alk (X, $R^1$, $R^2$ and Alk being as defined above and Y being a halogen atom, a protected hydroxyl group, e.g. of formula $OR^4$ or a group of the formula SH, $SR^4$, $SOR^4$, $SO_2R^4$, $NH_2$, $NHR^4$, or $NR^4R^5$, wherein $R^4$ is an alkyl, aralkyl or aryl group or trialkylsilyl group and $R^5$ is a group as defined for $R^4$, or $R^4$ and $R^5$ together with the nitrogen atoom to which they are attached from a heterocyclic ring). It will be appreciated that when Y is other than SH and one nitrogen carries a group Alk, the compound of formula IX will be a quaternary ammonium compound in association with an anion; when Y is SH the compound of formula IX normally exists in the thione form and the nitrogen carrying the group Alk is tertiary. When Y is replaced by OH, the resulting product exists as a lactam of formula I. Replacement of the substituent Y can be effected by reaction of the compound of formula IX or its quaternary derivative under acid or alkaline hydrolytic conditions for example, in aqueous mineral acid or a hydroxide e.g. an alkali metal hydroxide such as potassium hydroxide. The reaction may, for example, be effected in aqueous alcoholic or alcoholic solvents. Alkyl, aralkyl, aryl and acyl groups in $R^4$ preferably contain 1–8 carbon atoms, where $R^4$ and $R^5$ form a ring, thus preferably contains 5–7 carbon atoms and may contain one or more other heteroatoms. Methods of preparing compounds of formula IX are described hereinafter.

In the case of quaternary derivatives of compounds of formula IX in which Y is $OR^4$, conversion of a compound of formula I can alternatively be effected by reaction with anionic nucleophiles in particular halide ions such as $I^-$. Consequently when a compound of formula IX in which Y is $OR^4$ is converted into a quaternary derivative by reaction with an alkylating agent such as an alkyl iodide, cleavage of the the O-R bond is commonly effected to yield a lactam of formula I.

(g) reaction of a compound of the formula

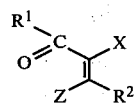

(where X, $R^1$ and $R^2$ have the above meanings and Z is a halogen atom or OH, $OR^4$, $SR^4$, $NH_2$, $NHR^4$ or $NR^4R^5$, where $R^4$ and $R^5$ have the above meanings) with a reagent or reagents serving to replace Z and the oxo group of formula $R^1CO$ by a urea moiety —$NR^3$-,$CO,NR^3$— where $R^3$ has the above meaning, at least one of the groups $R^3$ being hydrogen.

In one variation, the compound of formula X is reacted with a urea derivative of the formula

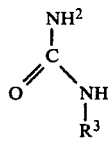

(where $R^3$ has the above meaning).

The product of the reaction may comprise one or both of the isomers

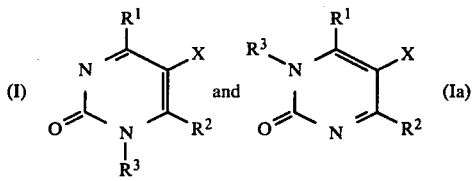

but since the definations of $R^1$ and $R^2$ are identical, compound Ia is, in fact, a compound of formula I.

The reaction of the compounds of formula X and XI can be effected by under acid conditions, preferably in a solvent such as an alcohol, e.g. ethanol. The reaction proceeds at room temperature in the case where $R^1$ and $R^2$ are both hydrogen and Y is OH, i.e. using a halogeno-malondialdehyde.

When Z is a group $NHR^4$, the possibility exists that in the reaction with the urea of formula XI, the group $NHR^3$ of the urea will eliminate rather than $NHR^4$; the product will, however, still be a compound of formula I since $R^4$ falls within the definition of $R^3$.

This general reaction can also be used to prepare starting materials of formula II for reaction (a) by selecting corresponding compounds of formula X in which X is hydrogen.

Similarly, starting materials of formula IX for use in reaction (f) may be prepared by replacing the urea derivative of formula XI by a corresponding isourea, thiourea, isothiourea or guanidine compound which may be represented by the formula

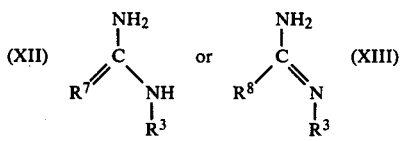

(wherein $R^7$ is =S or =$NR^3$ and $R^8$ is $OR^4$ or $SR^4$ where $R^4$ has the above meaning); the compound of formula XIII may be in the form of an acid addition salt, e.g. a hydrohalide.

The urea reagent of formula XI may be replaced by a cyanamide of formula $R^3NH.C\equiv N$ which reacts to form an intermediate of the formula

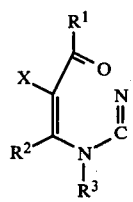

which may readily be cyclised in the presence of water to yield a product of formula I.

In other variation Z in the compound of formula X may be $-NH_2$ or $-NHR^4$, that is the compound may have the formula

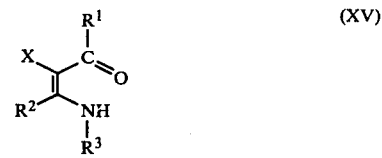

(wherein, X, $R^1$, $R^2$ and $R^3$ have the above meanings) and may be reacted as the base or an addition salt thereof, with a reagent or reagents serving to replace the oxo group of formula $R^1CO-$ and the hydrogen of $R^3NH-$ by a grouping $CO.NH.R^3$ wherein at least one group $R^3$ is hydrogen. Such a reagent or reagents react initially either at the $-NHR^3$ grouping to form a ureide or at the carbonyl group to form an aminocarbinol or Schiff's base. In each case, however, ring-closure is subsequently effected by reaction between the unreacted pair of groups. When one of the groups $R^3$ is hydrogen and the other Alk, the groups Alk will be vicinal either to $R^1$ or $R^2$ but in both cases the eventual ring compound will be of formula I.

The reagent reacted with compound XV may, for example, be cyanic acid, an isocyanate $R^3NCO$, or a carbamoyl ester or thioester, halide or anhydride which can effect ring-closure directly, or a carbonyl dihalide, oxalylhalide or haloformate ester or carbonate diester which converts an amine to a carbamoyl derivative or isocyanate which may then be reacted with ammonia or an amine, to effect ring closure; alternatively the ammonia or amine may be reacted initially with the carbamoyl grouping or the carbonyl grouping but the resulting product may readily be ring-closed to produce a product of formula I.

Similarly it is possible to react the compound of formula XV directly with the amine of formula $R^3NH$ to form an aminocarbinol or Schiff's base which may then be reacted with a carbonyl dihalide, a haloformate ester or thioester or a carbonic acid diester. Alternatively, ring closure can be effected by reaction of the aminocarbinol or Schiff's base with carbon monoxide in the present of sulphur in a solvent such as methanol.

In another variation an amminocarbinol or Schiff's base of the formula

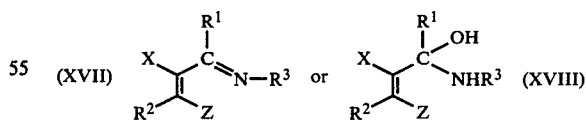

(where $R^1$, $R^2$, $R^3$, X and Z have the above meanings) may be reacted with carbamic acid ester or halide or, where Z is halogen, $OR^4$, $SR^4$, $NR^4R^5$ with cyanic acid or a salt thereof, to replace Z by a group $NR^3.R^{10}$ (where $R^{10}$ is an esterified carboxyl group or halocarbonyl group) or by an isocyanate group which then reacts with Schiff's base on amino carbinol grouping to effect ring closure. Alternatively, reaction may take place initially at the Schiff's base or amminocarbinol grouping and ring closure take place by replacement of Z.

In another variation amminocarbonyl compounds of formula XV may be reacted with a cyanogen halide to form an intermedicle of formula X which can then undergo cyclisation in the presence of water. In a still further variation a compound of formula X as defined above may be reacted with a carbamate ester, or cyanic acid or a salt thereof to yield a product having a carbamoyl or isocyanate group in place of the group Z which can then be reacted with an amine $R^3NH$ where $R^3$ has the above meaning with eventual cyclisation to yield a compound of formula I. If the nitrogen atom of the carbamate also carries a group Alk as defined above, $R^3$ in the amine $R^3NH$ should be hydrogen.

A wide variety of reactions may be effected in order to interconvert the various possible sidechains. For example, when Alk— represents an alkyl group substituted by one or more hydroxyl groups, the hydroxyl group may be replaced by one or more halogen atoms by treatment with a halogenating reagent serving to replace hydroxyl by halogen for example, a phosphorus halide or oxyhalide e.g. $PBr_3$, $POCl_3$, or $PCl_3$, or other acidic non-metal halide such as thionylchloride; the resulting compounds which include halogen atoms in the Alk— side-chain may, if desired, be subsequently subjected to hydrogen halide elimination to produce alkenyl or alkynyl groups, or amination reactions in order to produce amines. These reactions may all be effected by conventional means provided other groups in the molecule are not affected. In particular it may be desirable to select substituents in groups Alk present in the 1-, 4- and/or 6-portions which will not be significantly reactive in the above-described preparative procedures (a) to (g). It will further be appreciated that the particular reaction from methods (a) to (g) which is selected may in part be influenced by the nature of any substituents required in $R^1$, $R^2$ and/or $R^3$.

According to a further aspect of the invention, we provide pharmaceutical compositions comprising one or more compounds of general formula I as defined above, or salts or esters thereof, together with a pharmaceutical carrier or excipient.

The agents may be formed for pharmaceutical administration in any suitable manner. Thus, compositions will normally be in the form suitable for oral or parenteral administration, such as tablets, capsules, granules and solutions, for ingestion by the gastro-intestinal tract, or sterile injectible solutions in pyrogen-free water. The compositions will generally be administered at a daily dose level in the range 0.5 to 5.0 g of the compound of the invention; the compositions will conveniently be formulated in dosage units, each dosage unit typically containing from 100 mg to 1.0 g of the compound of the invention, though units containing as much as 5 g may occasionally be suitable.

Conventional carrier and excipient ingredients may be used, such as talc, gum arabic, lactose, starch, magnesium stearate, cocoa butter, animal and vegetable fats, paraffin derivatives, glycols, propellants, and various wetting, dispersing, emulsifying, flavouring and preserving agents.

The compounds of the invention may be formulated in compositions together with other chemotherapeutic agents, for example, cytosine arabinoside. This has been found a good partner for metaphase inhibitors in view of the combined effect the two compounds have on the cell growth pattern.

The invention will now be more particularly described in the following Examples, which are by way of illustration only. Many of the starting compounds have been prepared-prior art publications and reference numbers are given when appropriate as follows:

EXAMPLE 1

1-Methyl-5-fluoropyrimid-2-one

A mixture of the potassium salt of 5-fluoropyrimid-2-one (prepared as described in Undeheim, K. and Gacek, M. Acta. Chem. Scand. 23 (1969) 294 or Budesinsky, Z., Prikyl, J. and Svatek, E. Coll. Czech. Chem. Commun. 30 (1965) 3895) (0.01 mol) and methyl iodide (0.013 mol) in dimethylformamide (40 ml) was stirred at room temperature for 20 hours. The solvent was then removed under reduced pressure (1 mm Hg) and the said residue triturated with chloroform (4×50 ml). The chloroform solution containing the desired product was washed with aqueous 1 N NaOH (3 ml) and with water (3 ml). The dried ($MgSO_4$) chloroform solution was then evaporated and the solid residue recrystallised from benzene; yield 40%, m.p.=177°–178° C. (Found: C, 47.21; H, 3.95; Calc. for $C_5H_5FN_2O$: C, 46.88; H, 3.93)

EXAMPLE 2

1-Methyl-5-chloropyrimid-2-one

1-Methyl-5-chloropyrimid-2-one was prepared as above from the potassium salt of 5-chloropyrimid-2-one (prepared as described in Crosby, G. D. and Berthold, V. R. J. Org. Chem. 25 (1960) 1916) in 50% yield, m.p. 210° C. (acetone). (Found: C, 41.61; H, 3.65; Calc. for $C_5H_5ClN_2O$: C, 41.54; H, 3.48)

EXAMPLE 3

1-Propyl-5-fluoropyrimid-2-one

1-Propyl-5-fluoropyrimid-2-one was prepared as above from the potassium salt of 5-fluoropyrimid-2-one and n-propyl iodide in 20% yield after 48 hours; m.p. =93° C. (ligroin). (Found: C, 54.04; H, 5.82; Calc for $C_7H_9FN_2O$: C, 53.86; H, 5.81).

EXAMPLE 4

1-(2-Hydroxyethyl)-5-fluoropyrimid-2-one

5-Fluoropyrimid-2-one (0.008 mol) was dissolved in a solution of potassium hydroxide (0.008 mol) in absolute ethanol (100 ml) at 80° C. and ethylene bromohydrin (0.008 mol) added gradually with stirring. The alkylation was incomplete when the pH had become neutral. The reaction was further monitored by chromatography and equivalent amounts of potassium hydroxide and ethylene bromohydrin added until all the pyrimidine had been alkylated. The reaction mixture was then filtered and the filtrate evaporated to dryness before the residue was triturated with ether and extracted with warm acetone. Evaporation of the acetone solution left the title compound in 50% yield, m.p. 134°–136° C. after recrystallisation from ethanol; Found: C, 45.83; H, 4.42; Calc. for $C_6H_7FN_2O_2$: C, 45.58; H, 4.46.

EXAMPLE 5

1-(2-Hydroxyethyl)-5-chloropyrimid-2-one was obtained as above from 5-chloropyrimid-2-one in 60% yield, m.p. 170°–171° C. (isopropanol).

(Found: C, 41.33; H, 4.10; Calc. for $C_6H_7ClN_2O_2$: C, 41.27; H, 4.04.

EXAMPLE 6

1-(2-hydroxyethyl)-5-bromopyrimid-2-one 1-(2-hydroxyethyl)-5-bromopyrimid-2-one was prepared from 5-bromopyrimid-2-one as described above. The hot reaction mixture, when the alkylation reaction was complete was filtered. The solid precipitate formed in the cold filtrate was collected and extracted with boiling ethanol (2×25 ml) and the ethanol extracts combined and evaporated to dryness. The title compound was then extracted with boiling isopropanol from which it crystallised on cooling; yield 71%; m.p. 177°–179° C. (Found: C, 33.12; H, 3.38. Calc for $C_6H_7BrN_2O_2$: C, 32.90; H, 3.22).

EXAMPLE 7

1-(2,3-Dihydroxypropyl)-5-chloropyrimid-2-one

A solution prepared from 5-chloropyrimid-2-one (0.02 mol) potassium hydroxide (0.02 mol), and 3-chloro-1,2-propanediol (0.02 mol) in abs. ethanol (160 ml) was heated under reflux until neutral pH. The warm reaction mixture was filtered before concentration to a small volume at reduced pressure. The syrupy precipitate was partially crystallised on standing in the cold. The oily material was removed from the crystalline material by suction on a filter and the crystalline material recrystallised from acetonitrile, yield 32% m.p. 136°–138° C.; (Found: C, 41.15; H, 4.55; Calc. for $C_7H_9ClN_2O_3$: C, 41.09; H, 4.43).

EXAMPLE 8

1-(1-O-Methyl-2,3-O-isopropylidene-5-D-ribofuranosyl-5-chloropyrimid-2-one

Methyl-2,3-$\underline{O}$-isopropylidene-5-$\underline{O}$-tosyl-D-furanoside (0.01 mol) and the potassium salt of 5-chloropyrimid-2-one (0.008 mol) were heated together in DMF (60 ml) with stirring at 80° C. for 24 hours. The solvent was then evaporated at reduced pressure (1 mm Hg), the residue was extracted with chloroform (100 ml). The chloroform solution was washed with aqueous 2 N NaOH (3 ml), with water (3 ml) and dried over MgSO4 before evaporation to dryness. The residue was washed with pet.ether and ether and was recrystallised from ispropanol; yield 32%, m.p. =189° C.
$[\alpha]_D = +11.9$ (c=1.0 in MeOH). (Found: C, 49.43; H, 5.43; Calc. for $C_{13}H_{17}ClN_2O_5$: C, 49.30; H, 5.41).

EXAMPLE 9

1-(5-D-ribofuranosyl)-5-chloropyrimid-2-one 1-(1-$\underline{O}$-Methyl-2,3-$\underline{O}$-isopropylidene-5-D-ribofuranosyl)-5-chloropyrimid-2-one (0.0045 mol) was dissolved in trifluoroacetic acid (9 ml) and water (1 ml) and the solution left at room temperature for 48 hours. After evaporation at reduced pressure, the residue was triturated with ether and recrystallised from dioxan/Et2O; yield 85%, m.p. gradual decomposition from ca. 75° C. (Found: C, 41.64; H, 4.58. Calc. for $C_9H_{11}ClN_2O_5$: C, 41.15; H, 4.22).
$[\alpha]_D = +73.8$ (C=0.5 in 50% isopropanol).

EXAMPLE 10

1-(2-Desoxy-2-acetylamino-3,4,6-tri-$\underline{O}$-acetyl-D-glucopyranosyl)-5-chloropyrimid-2-one 2-Desoxy-2-acetylamino-3,4,6-tri-O-actyl-D-glucopyranosylchloride (0.01 mol) and the potassium salt of 5-chloropyrimid-2-one (0.008 mol) were heated together in dimethylformamide (60 ml) with stirring at 80° C. for 24 hours. The solvent was then evaporated at reduced pressure (1 mm Hg) and the residue was extracted with chloroform (120 ml). The chloroform solution was washed with aqueous 1 N NaOH (2×3 ml) and water (3 ml) before drying (Mg SO4). Evaporation left the title compound which was further purified by trituration with ether and recrystallization from a small volume of methanol; yield 50%, m.p. 165°–167° C. when the sample is heated rapidly. (Found: C, 47.00; H, 4.82. Calc. for $C_{18}H_{22}ClN_3O_9$: C, 47.02; H, 4.82)
$[\alpha]_D = +9.0°$ (c=0.5 in methanol)

EXAMPLE 11

1-(2-Desoxy-2-acetylamino-D-glucopyranosyl)-5-chloropyrimid-2-one 1-(2-Desoxy-2-acetylamino-3,4,6-tri-O-acetyl-1-D-glucopyranosyl)-5-chloropyrimid-2-one (0.0052 mol) was added to a solution of sodium methoxide (0.0012 mol) in methanol (15 ml) and the resultat solution left at room temperature for 1 hour. A strong cation exchange (Dowex 50 W,H+; 4 ml) was then added and the mixture was stirred well before filtration. The filtrate was evaporated and the residue was made to crystallise by trituration with ether. The product was further purified by recrystallisation from ethanol; yield 45%, m.p. 156°–158°. (Found: C, 43.00; H, 4.90. Calc. for $C_{12}H_{16}ClN_3O_6$: C, 43.20; H, 4.83).
$[\alpha]_D = -16.6°$ (c=0.5 in methanol)

EXAMPLE 12

1-(2-chloroethyl)-5-chloropyrimid-2-one 1-(2-Hydroxyethyl)-5-chloropyrimid-2-one (0.001 mol) and phosphorus oxychloride (5 ml) were heated together at 80° C. for 60 min. before the solution was evaporated at reduced pressure. The residue was triturated with chloroform before dissolution in water (4 ml) and neutralisation with sodium bicarbonate. Chloroform extraction and evaporation left a solid which was recrystallised from ethyl acetate, yield 52%, m.p. 167°–168° C. (Found: C, 37.20; H, 3.20; Calc for $C_6H_6Cl_2N_2O$: C, 37.34; H 3.13).

EXAMPLE 13

1-(2-Chloroethyl)-5-bromopyrimid-2-one 1-(2-Hydroxyethyl)-5-bromopyrimid-2-one (0.012 mol) was added to ice-cold phosphorus oxychloride (60 ml) and the mixture was stirred for 15 min in the cold after which it was slowly heated to 80° C. (oil-bath) and kept at this temperature for 1 h. The reaction mixture was then evaporated to dryness at reduced pressure. The residue was triturated with chloroform (20 ml) before dissolution in water (20 ml). The aqueous solution was next neutralized with NaHCO3 and extracted with chloroform (4×50 ml). Evaporation of the combined and dried (MgSO4) chloroform extracts left the title compound in 65% yield, m.p. 185°–186° C. (ethyl acetate). (Found: C, 30.58; H, 2.62. Calc. for $C_6H_6BrClN_2O$: C, 30.34; H, 2.54).

EXAMPLE 14

1-(Hydroxy-3-chloropropyl)-5-bromopyrimid-2-one

A mixture of 5-bromopyrimid-2-one (0.018 mol), 1-chloro-2,3-epoxypropane (0.018 mol) and potassium carbonate (40 mg) in dimethylformamide (80 ml) was heated with stirring at 80° C. for 20 h. The cold reaction mixture was filtered and the filtrate was evaporated to dryness at reduced pressure (1 mm Hg). The residue was extracted with chloroform and the chloroform solution was washed with aqueous 1 N NaOH (3 ml), with water (5 ml) and dried (MgSO$_4$). The solution was then filtered through a column of neutral Al$_2$O$_3$ (Woelm, activity III); yield 33%., m.p. 162°–164° C. (acetone).

(Found: C, 31.61; H, 3.13. Calc. for C$_7$H$_8$BrClN$_2$O$_2$: C, 31.43; H, 3.01).

EXAMPLE 15

1-(2-Hydroxy-3-chloropropyl)-5-chloropyrimid-2-one

Prepared as above from 5-chloropyrimid-2-one in 20% yield, m.p. 159°–162° C. (acetone). (Found: C, 38.00; H, 3.51. Calc. for C$_7$H$_8$Cl$_2$N$_2$O$_2$: C, 37.69; H, 3.61).

EXAMPLE 16

1-(2-Hydroxy-3,3,3-trichloropropyl)-5-bromopyrimid-2-one

A stirred mixture of 5-bromopyrimid-2-one (0.009 mol), 1,2-epoxy-3,3,3-trichloropropane (0.009 mol) and K$_2$CO$_3$ (33 mg) in dimethylformamide (40 ml) was heated at 80° C. for 4 h. The reaction mixture was then evaporated to dryness at reduced pressure (1 mm Hg). The crystalline residue was triturated with a little ether and dissolved in ethyl acetate. The filtered ethyl acetate solution was concentrated to about 50 ml and left in the cold when the product crystallized out in 52% yield. m.p. 210°–212° C. (ethyl acetate).

(Found: C, 25.00; H, 1.59. Calc. for C$_7$H$_6$BrCl$_3$N$_2$O$_2$: C, 24.99; H, 1.79).

EXAMPLE 17

1-(2-Dimethylaminoethyl)-5-chloropyrimid-2-one

2-Dimethylaminoethyl chloride (0.016 mol) was added to the potassium salt of 5-chloropyrimid-2-one (0.012 mol) in dimethylformamide (50 ml) and the reaction mixture stirred at 80° C. for 7 h. The solvent was then evaporated at reduced pressure (1 mm Hg) and the residue was extracted with chloroform (150 ml). The chloroform solution was washed with 1 N NaOH (2×4 ml), with water (5 ml) and dried (MgSO$_4$) before evaporation. The product was recrystallized from benzene containing a little pet. ether; yield 47%, m.p. 157° C. (Found: C, 47.87; H, 6.05 Calc. for C$_8$H$_{12}$ClN$_3$O: C, 47.64; H, 5.99).

EXAMPLE 18

1-(2-Trimethylammonioethyl)-5-chloropyrimid-2-one iodide 1-(2-Dimethylaminoethyl)-5-chloropyrimid-2-one (0.004 mol) and methyl iodide (0.006 mol) were dissolved in acetonitrile (20 ml) and the reaction mixture was stirred at room temperature for 6 h. The precipitate was then collected, washed with ether and recrystallized by dissolving in boiling isopropanol (50 ml) to which water (in all 14 ml) was added dropwise, until dissolution was complete; yield 50%, m.p. 235° C. (decomp.). (Found: C, 31.34; H, 4.48. Calc. for C$_9$H$_{15}$ClIN$_3$O: C, 31.46; H, 4.40).

EXAMPLE 19

1-Allyl-5-fluoropyrimid-2-one

The sodium salt of 5-fluoropyrimid-2-one (0.01 mol) was dissolved in methanol (100 ml) and allyl bromide (0.015 mol) added gradually at room temperature and the reaction allowed to proceed until neutral pH had been reached. The reaction mixture was then concentrated at reduced pressure and the residue extracted with chloroform (100 ml). The chloroform solution was washed with water (2×5 ml) and dried before evaporation; Yield 48%, m.p. 88°–90° C. after recrystallisation from acetone: (Found: C, 55.10; H, 4.80. Calc. for C$_7$H$_7$FN$_2$O: C, 54.56; H, 4.58.

EXAMPLE 20

1-Allyl-5-chloropyrimid-2-one was prepared from 5-chloropyrimid-2-one as above in 64% yield. m.p. 130°–131° C. (acetone) (Found: C, 49.22; H, 4.13. Calc. for C$_7$H$_7$ClN$_2$O: C, 49.28; H, 4.13).

EXAMPLE 21

1-Allyl-5-bromopyrimid-2-one was prepared from 5-bromopyrimid-2-one as above in 40% yield m.p. 142°–143° C. (acetone)

(Found: C, 39.28; H, 3.43. Calc. for C$_7$H$_7$BrN$_2$O: C, 39.10; H, 3.28).

EXAMPLE 22

1-Propargyl-5-chloropyrimid-2-one

A mixture of the potassium salt of 5-chloropyrimid-2-one (0.009 mol) and propargyl bromide (0.013 mol) in dimethylformamide (40 ml) was stirred at room temperature for 18 h. The solvent was then removed at reduced pressure (1 mm Hg) and the residue was extracted with chloroform (150 ml). The chloroform solution was passed through a column of Al$_2$O$_3$ (Woelm; 30 g, activity III). Evaporation of the chloroform eluates left a solid which was triturated with a little ether before recrystallization from EtOAc; yield 56%, m.p. 130° C. (Found: C, 50.11; H, 2.95. Calc. for C$_7$H$_5$ClN$_2$O: C, 49.87; H, 2.99).

EXAMPLE 23

1-Propargyl-5-fluoropyrimid-2-one

Prepared as above from 5-fluoropyrimid-2-one in 30% yield, m.p. 107°–108° C. (benzene/ligroin). (Found: C, 55.55; H, 3.58. Calc. for C$_7$H$_5$FN$_2$O: C, 55.28; H, 3.31).

EXAMPLE 24

1-Propargyl-5-bromopyrimid-2-one

Prepared as above from 5-bromopyrimid-2-one in 60% yield; m.p. 139°–141° C. (ethyl acetate). (Found: C, 39.64; H, 2.47. Calc. for C$_7$H$_5$BrN$_2$O: C, 39.47; H, 2.36).

EXAMPLE 25

1-Benzyl-5-fluoropyrimid-2-one

Benzyl chloride (0.01 mol) was added to a stirred mixture of the potassium salt of 5-fluoropyrimid-2-one (0.007 mol) in dimethylformamide (40 ml) and the mixture stirred at room temperature until chromatography showed the reaction to be complete. The solvent was then evaporated at reduced presure (1 mm Hg) and the residue was extracted with chloroform (100 ml). The chloroform solution was washed with aqueous 2 N NaCH (2×3 ml) and with water (3 ml) before drying (MgSO₄) and evaporation; yield 50%, m.p. 163° C. (ethyl actate). (Found: C, 64.69; H, 4.49. Calc. for C₁₁H₉FN₂O: C, 64.70; H, 4.44).

EXAMPLE 26

1-Benzyl-5-chloropyrimid-2-one

Prepared as above from 5-chloropyrimid-2-one in 53% yield, m.p. 197° C. (ethyl acetate). (Found: C, 60.20; H, 4.20. Calc. for C₁₁H₉ClN₂O: C, 59.89; H, 4.11).

EXAMPLE 27

1-Carboxymethyl-5-chloropyrimid-2-one

A solution made from 5-chloropyrimid-2-one (0.015 mol), aqueous 0.78 M KOH (45 ml) and chloroacetic acid (0.018 mol) was heated under reflux until the pH had fallen to below 8. The solution was then concentrated to a small volume at reduced pressure. Addition of 1 N HCl (15 ml) caused the product to crystallize; yield 47%, m.p. 186°–188° C. (acetone). (Found: C, 38.35; H, 2.69. Calc. for C₆H₅ClN₂O₃: C, 38.23; H, 2.67).

EXAMPLE 28

1-Carboxymethyl-5-fluoropyrimid-2-one

Prepared as above from 5-fluoropyrimid-2-one in 67% yield, m.p. 200°–202° (decomp) (acetone/methanol). (Found: C, 41.80; H, 3.10. Calc. for C₆H₅FN₂O₃: C, 41.87; H, 2.93).

EXAMPLE 29

1-Carboxymethyl-5-bromopyrimid-2-one

Prepared as above from 5-bromopyrimid-2-one in 50% yield, m.p. 183°–185° C. (acetone). (Found: C, 30.85; H, 2.08. Calc. for C₆H₅BrN₂O₃: C, 30.93; H, 2.16).

EXAMPLE 30

1-Ethoxycarbonylmethyl-5-chloropyrimid-2-one

5-Chloropyrimid-2-one (0.02 mol) was added to a stirred solution of KOH (0.02 mol) in ethanol (100 ml) followed by addition of ethyl bromoacetate (0.023 mol). The reaction mixture was heated under reflux for 4 h. The reaction mixture was then evaporated to dryness at reduced pressure and the residue was extracted with chloroform (150 ml). The chloroform extract, after filtration, was washed with aqueous 0.5 N NaOH (2×3 ml) and water (3 ml). Evaporation of the dried (MgSO₄) solution left the product which was recrystallized from acetone; yield 39%, m.p. 175°–177° C. (Found: C 44.65; H, 4.17. Calc. for C₈H₉ClN₂O₃: C 44.36; H, 4.19).

EXAMPLE 31

1-Ethoxycarbonylmethyl-5-fluoropyrimid-2-one

Prepared as above from 5-fluoropyrimid-2-one in 31% yield, m.p. 121° (ethyl acetate). (Found: C, 47.90; H, 4.70. Calc. for C₈H₉FN₂O₃: C, 48.02; H, 4.53).

EXAMPLE 32

4-Methyl-5-chloropyrimid-2-one (a) 5-chloro-6-methyl-4-thiouracil

5-Chloro-6-methyluracil (prepared as described in Johnson, B. T. J. Amer. Chem. Soc. 65 (1943) (1220) (0.018 mol) and phosphorus pentasulphide (0.019 mol) were heated together in refluxing dioxan (200 ml) for 45 min. The hot reaction mixture was then filtered and the cold filtrate concentrated and diluted with ether. The participate collected after a few hours in the cold, was recrystallised from water; yield 75% m.p. 297°–300° C. (decomp.); (Found: C, 32.69; H, 3.96. Calc. for C₅H₅ClN₂OS.½H₂O: C, 32.35; H, 3.25).

(b) 4-Methyl-5-chloropyrimid-2-one

Conc. aqueous ammonia (200 ml) and sodium carbonate (0.012 mol) were added to Raney-Ni (20 g) in water (200 ml) followed by the addition of 5-chloro-6-methyl-4-thiouracil (0.023 mol). The reaction mixture was stirred at room temperature for 1 hr and then heated under reflux for 3 hr. The catalyst was removed from the cold reaction mixture and the filtrate evaporated. The residual material was stirred in 5 N NaOH (20 ml) and the sodium salt filtered off from the ice-cold mixture and washed with abs. ethanol and acetone. The product was recrystallised from aqueous ethanol; yield 53%, m.p. 300° C. (decomp.); For elemental analysis the sodium salt in aqueous solution was neutralised with HCl. Found: C, 41.40; H, 3.60. Calc. for C₅H₅ClN₂O: C, 41.54; H, 3.48.

EXAMPLE 33

4-Methyl-5-bromopyrimid-2-one

Bromine (0.004 mol) was added to an aqueous solution (20 ml) of 4-methylpyrimid-2-one (0.002 mol). The reaction mixture was left at room temperature for 4 h before evaporation. The residue was triturated with acetone and recrystallised from acetic acid; yield 80%, m.p. (Found: C, 22.2; H, 2.3; Br, 59.2. Calc. for C₅H₅N₂OBr. HBr: C, 22.2; H, 2.22; Br, 59.25).

EXAMPLE 34

1,4-Dimethyl-5-chloropyrimid-2-one

A solution of the sodium salt of 4-methyl-5-chloropyrimid-2-one (0.005 mol) and methyl iodide (0.0055 mol) in abs. ethanol (70 ml) was heated under reflux until ca. neutral pH. Another 0.005 mol of potassium hydroxide and methyl iodide were added and the heating continued to ca. neutral pH. The reaction mixture was then filtered and the filtrate evaporated to dryness. The residual material was repeatedly extracted with chloroform and the chloroform extracts evaporated and the solid extract recrystallised from isopropanol; yield 35%, m.p. 132°–134° C. (Found: C, 45.51; H, 4.51. Calc. for C₆H₇ClN₂O: C, 45.44; H, 4.43).

EXAMPLE 35

1,4-Dimethyl-5-bromopyrimid-2-one

Bromine (0.012 mol) was added to an aqueous solution (100 ml) of 1,4-dimethylpyrimid-2-one (0.008 mole) and the reaction mixture left at room temperature for 3 hr before freeze-drying. The residual material was triturated with acetone and recrystallised from water; yield 40%, m.p. 170° C. (decomp.). (Found: C, 25.5; H, 2.9. Calc. for C₆H₇BrN₂O HBr: C, 24.4; H, 2.8).

EXAMPLE 36

4,6-Dimethyl-5-chloropyrimid-2-one

A solution of chlorine (0.01 mol) in acetic anhydride (100 ml) was added to a solution of 4,6-dimethylpyrimid-2-one (0.008 mol) in acetic anhydride (100 ml) and the solution left at room temperature for 1 hr before the solid precipitate was collected and recrystallised from water; m.p. 235° C. (decomp.)

(Found: C, 37.1; H, 4.1; Cl, 36.6. Calc. for $C_6H_7ClN_2OHCl$: C, 37.1; H, 4.1, Cl, 35.9).

EXAMPLE 37

4,6-Dimethyl-5-bromopyrimid-2-one

Bromine (0.025 mol) was added to a solution of 4,6-dimethylpyrimid-2-one (0.02 mol) in water (400 ml) at 50° C. The reaction mixture was left for 2 hr at room temperature and freeze-dried and the residue triturated with acetone and recrystallised from aqueous ethanol: yield 40%, m.p. 220° C. (decomp.).

(Found: C, 25.5; H, 2.7. Calc. for $C_6H_7BrN_2O$. HBr: C, 25.4; H, 2.8).

EXAMPLE 38

1,4,5-Trimethyl-5-bromopyrimid-2-one

Bromine (0.009 mol) was added to a solution of 1,4,6-trimethylpyrimid-2-one (0.006 mol) in water (100 ml) and the mixture stirred at room temperature for 2 hr. before freeze-drying. The residue was triturated with acetone and recrystallised from ethanol; m.p. 225° C. (decomp.) (Found: C, 27.8; H, 3.3. Calc. for $C_7H_9BrN_2O$: C, 28.2; H, 3.4).

EXAMPLE 39

4-Methylthio-5-fluoropyrimid-2-one

Prepared according to the method of Ueda and Fox J. Med. Chem. 6, (1963), 679.

EXAMPLE 40

4-Methylthio-5-chloropyrimid-2-one

5-Chloro-4-thiouracil (0.0027 mol) was dissolved in 1 M sodium hydride (3 ml) and methyl iodide (0.007 mol) added. The solution was stirred at room temperature for 3 hr. and the solid precipitate collected and recrystallised from water; yield 21%, m.p. 254° C.

(Found: C, 33,90; H, 2.70. Calc. for $C_5H_5ClN_2OS$: C, 34.00; H, 2.85).

EXAMPLE 41

4-Methylthio-5-bromopyrimid-2-one

4-Methylthiopyrimid-2-one (prepared as described in Wheller, L. H. and Johnson, B. T. J. Amer. Chem. Soc. 42 (1909) (30), (0.01 mol) was dissolved at ca. 80° C. in acetic acid (30 ml) containing 2% acetic anhydride. The temperature was lowered to ca. 55° C. and N-bromosuccinimide (0.013 mol) added and the reaction mixture stirred at this temperature for 40 min. Ice-cold water (150 ml) containing a little sodium bisulphite was then added and the precipitated collected and recrystallised from water; yield 28%, m.p. 260° C.;

(Found: C, 25.76; H, 2.65. Calc. for $C_5H_5BrN_2OS$.$H_2O$: C, 25.11; H, 2.95).

EXAMPLE 42

4-Ethylthio-5-fluoropyrimid-2-one

(a) 5-Fluoro-4-thiouracil

Prepared from 5-fluorouracil by the method of Ueda and Fox (see above) using phosphorus pentasulphide in pyridine. We find that dioxan is a better solvent in this reaction in which case the yield was 80% of a more pure product.

(b) 4-Ethylthio-5-fluoropyrimid-2-one

The potassium salt of 5-fluoro-4-thiouracil (0.0065 mol) and ethyl iodide (0.014 mol) in methanol (40 ml) were stirred at room temperature for 6 days. The solutions were concentrated at reduced pressure and water (6 ml) added. The slowly precipitated product was recrystallised from water; yield 70%, m.p. 168° C.

(Found: C, 41.20; H, 4.03; Calc. for $C_6H_7FN_2SO$: C, 41.37; H, 4.05).

EXAMPLE 43

4-Butylthio-5-fluoropyrimid-2-one n-Butyl bromide (0.007 mol) was added to a solution of the potassium salt of 5-fluoro-4-thiouracil (0.006 mol) in dimethylformamide (30 ml) and the reaction mixture was stirred at room temperature for 3 days before evaporation at reduced pressure (1 mm Hg). The desired product was isolated from the residue by preparative paper chromatography (Whatman No. 3) using butanol:ethanol:ammonia:water (4:1:2:1); yield 20%, m.p. 113° C. ($H_2O$). (Found: C, 47.20; H, 5.30. Calc. for $C_8H_{11}FN_2OS$: C, 47.52; H, 5.48).

EXAMPLE 44

4-Carboxymethylthio-5-fluoropyrimid-2-one

4-Ethoxycarbonylmethylthio-5-fluoropyrimid-2-one (0.0013 mol) in 2 M potassium hydroxide (4 ml) was heated on a waterbath for 5-6 min. The solution was allowed to cool before neutralisation with dilute hydrochloric acid. The precipitated solid was recrystallised from methanol: yield 41%, m.p. 255° C.

(Found: C, 35.10; H, 2.50. Calc. for $C_6H_5FN_2O_3S$: C, 35.29; H, 2.47).

EXAMPLE 45

4-Ethoxycarbonylmethylthio-5-fluoropyrimid-2-one

A solution of the sodium salt of 5-fluoro-4-thiouracil (0.0195 mol) and ethyl chloroacetate (0.0195 mol) in ethanol (50 ml) was heated under reflux for 2 hr. The solvent was removed at reduced pressure triturated with cold water and the residue recrystallised from water; yield 29%; m.p. 156° C. (Found: C, 41.38; H, 4.12. Calc for $C_8H_9FN_2O_3S$: C, 41.38; H, 3.90).

EXAMPLE 46

1-Methyl-4-methylthio-5-fluoropyrimid-2-one

Methyl iodide (0.017 mol) was added to the potassium salt of 4-methylthio-5-fluoropyrimid-2-one (0.012 mol) in dimethylformamide (50 ml) and the reaction mixture was stirred at room temperature for 24 h before evaporation at reduced pressure (1 mm Hg). The residue was extracted with chloroform and the solution was washed with aqueous 2 N NaOH, with water and was dried ($MgSO_4$) before evaporation. The product was recrystallized from EtOAc/ligroin; yield 76%, m.p. 154° C. (Found: C, 41.48; H, 4.10. Calc. for $C_6H_7FN_2OS$: C, 41.37; H, 4.05).

EXAMPLE 47

1-Carboxymethyl-4-methylthio-5-fluoropyrimid-2-one

4-Methylthio-5-fluoropyrimid-2-one (0.01 mol) was added to 2 M potassium hydroxide solution (10 ml) and dissolved. Chloroacetic acid (0.01 mol) was then added and the reaction mixture heated under reflux for 60 min when the pH was close to neutral. Some precipitate was removed by filtration from the cold reaction mixture and the filtrate brought to pH 2 with HCl. The precipitated product was recrystallised from aqueous methanol; yield 36%, m.p. 244°–245° C.

(Found: C, 38.68; H, 3.58. Calc. for $C_7H_7FN_2O_3S$: C, 38.53; H, 3.23).

EXAMPLE 48

1-Carboxymethyl-4-methylthio-5-bromopyrimid-2-one

Prepared from 4-methylthio-5-bromo-pyrimid-2-one as above in 77% yield; m.p. 238° C. (decomp.) after recrystallisation from aqueous methanol. (Found: C, 30.10; H, 2.70. Calc. for $C_7H_7BrN_2O_3S$: C, 30.12; H, 2.53).

EXAMPLE 49

1-(2-Hydroxyethyl)-4-methylthio-5-fluoropyrimid-2-one

Ethylene bromohydrin (0.023 mol) was added to a solution of the potassium salt of 4-methylthio-5-fluoropyrimid-2-one (0.015 mol) in dimethylformamide (65 ml) and the reaction mixture was stirred at room temperature for 24 h before evaporation at reduced pressure (1 mm Hg). The residue was extracted with chloroform, the solution was washed with aqueous 2 N NaOH, with water and was dried ($MgSO_4$) before evaporation. The solid residue was recrystallized from acetone; yield 77%, m.p. 161°–162° C. (Found: C, 41.36; H, 4.62. Calc. for $C_7H_9FN_2O_2S$: C, 41.17; H, 4.44).

EXAMPLE 50

1-Propargyl-4-propargylthio-5-fluoropyrimid-2-one

Propargyl bromide (0.025 mol) was added to the dipotassium salt of 4-thio-5-fluorouracil (0.01 mol) in dimethylformamide (40 ml) and the reaction mixture was stirred at room temperature for 48 h before evaporation at reduced pressure (1 mm Hg). The residue was extracted with chloroform, the solution was washed with aqueous 2 N NaOH, with water and was dried ($MgSO_4$) before evaporation. The solid residue was recrystallized from ethyl acetate; Yield 59%, m.p. 135° C. (Found: C, 53.86; H, 3.15. Calc. for $C_{10}H_7FN_2OS$: C, 54.03; H, 3.17).

EXAMPLE 51

4-Methylthio-5-bromo-6-methylpyrimid-2-one

4-Methylthio-6-methylpyrimid-2-one (see Wheeler, L. H. and MacFarland, F. D. J. Amer. Chem. Soc. 42 (1909) (43) (0.01 mol) was dissolved in acetic acid (30 ml) containing 2% acetic anhydride and N-bromo-succinimide (0.013 mol) added. The reaction mixture was kept at 55° C. for 40 min. Ice-cold water (150 ml) containing a little sodium bisulphite was added to the cold reaction mixture. The precipitate formed was recrystallised from water; yield 35%, m.p. 244° C. (Found: C, 30.34; H, 2.81. Calc. for $C_6H_7BrN_2OS$: C, 30.65; H, 3.00).

EXAMPLE 52

6-Methyl-4-methylthio-5-chloropyrimid-2-one

Methyl iodide (0.012 mol) was added to an aqueous solution prepared from 5-chloro-6-methyl-4-thiouracil (0.01 mol) and 0.725 M KOH (25 ml) and the reaction mixture was stirred at room temperature for 5 h. The solid precipitate formed was collected and was recrystallized from isopropanol; yield 65%, m.p. 268°.

(Found: C, 37.50; H, 3.90. Calc. for $C_6H_7ClN_2OS$: C, 37.79; H, 3.70).

EXAMPLE 53

1-Methyl-5-chloropyrimid-2-one

A mixture of 2-chloro-1,1,3,3-tetramethoxypropane (0.05 mol), N-methylurea (0.04 mol) in 10 N HCl (10 ml) in ethanol (100 ml) was allowed to stand at room temperature for 4 days. The reaction mixture was then evaporated, the residue dissolved in water (100 ml) and the pH of the solution adjusted to 8 by means of $Na_2CO_3$. The mixture was then extracted with chloroform (4×30 ml) and the dried ($Na_2SO_4$) extracts evaporated. The residue was recrystallised from acetone; yield 20%. The physical data for the product was identical to those measured for the compound as prepared by the method of Example 2.

EXAMPLE 54

1-Methyl-5-bromopyrimid-2-one

Prepared as above using 2-bromo-1,1,3,3-tetramethoxypropane; yield 16%.

EXAMPLE 55

1-(3-Chloroallyl)-5-chloropyrimid-2-one

A mixture of the potassium salt of 5-chloropyrimid-2-one (0.01 mol) and 1.3-dichloropropane (0.02 mol) in dimethylformamide (50 ml) was heated at 60° C. for 8 h. The reaction mixture was then evaporated (1 mm Hg) and the residue dissolved in chloroform (80 ml). This solution was washed with 1 N NaOH (2 ml) and water before drying and evaporation; yield 60%, m.p. 102°–104° C. (benzene/ligroin). (Found: C, 41.83; H, 3.02. Calc. for $C_7H_6ClN_2O$: C, 41.01; H, 2.95).

EXAMPLE 56

1-(3-Chloroallyl)-5-bromopyrimid-2-one

Prepared as above from 5-bromopyrimid-2-one in 45% yield, m.p. 114°–116° C. (benzene). (Found: C, 33.56; H, 2.62. Calc. for $C_7H_6BrClN_2O$: C, 33.70; H, 2.42).

EXAMPLE 57

1-(3-Butenyl)-5-bromopyrimid-2-one

A mixture of the potassium salt of 5-bromopyrimid-2-one (0.01 mol) and 4-bromo-1-butene (0.015 mol) was heated in methanol (60 ml) at 70° C. for 40 h. The reaction mixture was then evaporated and the mixture extracted with chloroform. This solution was washed with 1 N NaOH (5 ml). with water (5 ml) and dried ($MgSO_4$) before evaporating; yield 50%, m.p. 127°–128° C. (acetone). (Found: C, 42.06; H, 3.94. Calc. for $C_8H_9BrN_2O$: C, 41.94; H, 3.96).

EXAMPLE 58

1-Propargyl-4-methylthio-5-fluoropyrimid-2-one

The potassium salt of 4-methylthio-5-fluoropyrimid-2-one (0.005 mol) and propargyl bromide (0.06 mol) were stirred together in dimethylformamide (20 ml) for 40 hrs at room temperature. The mixture was then filtered; the filtrate evaporated at reduced pressure (1 mm Hg) and the residue extracted with chloroform (60 ml). The chloroform solution was washed with 1 N NaOH, with water, and dried ($MgSO_4$) before evaporation;

yield 71%, m.p. 101°–102° C. (ethyl acetate). (Found: C, 48.50; H, 3.62. Calc. for $C_8H_7SN_2O$: C, 48.48; H, 3.56).

EXAMPLE 59

4-Allylthio-5-fluoropyrimid-2-one

Allyl bromide (0.013 mol) was added to a solution of 5-fluoro-4-thiouracil (0.01 mols), 8.73 mols NaOH (25 mls) and the reaction mixture stirred at room temperature for 5 hrs. The reaction mixture was then extracted with chloroform (2×5 ml), before the aqueous solution was acidified with HCl when the titled compound was precipitated; yield 40%, m.p. 150°–152° C. (water). (Found: C, 44.87; H, 3.84. Calc. for $C_7H_7SFN_2O$; C, 45.15; H, 3.80).

EXAMPLE 60

4-Methyl-5-chloropyrimid-2-one (a) 2-methylthio-4,5-dichloro-6-methylpyrimidine 2-methylthio-5-chloro-6-methyluracil (0.075 mols) and phosphorus oxychloride (100 ml) were reacted together under reflux for 2 hrs. Most of the phosphorus oxychloride was removed under reduced pressure and the residue poured onto ice. The product was extracted into chloroform which was washed with saturated NaHCO$_3$ solution and dried (MgSO$_4$). The residue, of the separation, was recrystallised from pet. ether; yield 91% m.p. 49°–50° C.

(Found: C, 34.62%; H, 3.01%. Calc. $C_6H_6Cl_2N_2S$: C, 34.46; H, 2.89).

(b) 2-methylthio-5-chloro-6-methylpyrimide 2-methylthio-4,5-dichloro-6-methylpyrimidine (0.039 mols) and 5% palladium an charcoal (2.4 gms) were added to 0.67 M NaOH (167 ml) and the mixture hydrogenated at atmospheric pressure for 12 hrs. The catalyst was then removed by filtration and the filtrate repeatedly extracted with chloroform. Evaporation of the dried (MgSO$_4$) chloroform extract left the title compound which was purified by distillation; yield 55%. m.p. 126°–128° C. at 16 mm Hg. (Found: C, 41.20; H, 3.96. Calc. for $C_8H_7ClN_2S$: C, 41.26; H, 4.04).

(c) 4-methyl-5-chloropyrimid-2-one

A mixture of 2-methylthio-5-chloro-6-methylpyrimidine (0.01 mols) conc. HCl (12 ml) was heated under reflux for 100 mins. before evaporation at reduced pressure. The residue was triturated with acetone the substance recrystallised once from acetic acid and once from ethanol. Yield 72%/m.p. discoloration from about 180° C. with decomposition. (Found: C, 41.40; H, 3.60. Calc. for $C_5H_5ClN_2O$: C, 41.54; H, 3.48).

What we claim is:

1. A compound of the formula:

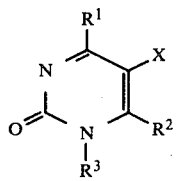

(I)

wherein X represents a fluorine, chlorine or bromine atom; $R^1$ and $R^2$, which may be the same or different, each represent hydrogen or a group Alk or SAlk; and $R^3$ represents a group Alk; Alk being an alkyl, alkenyl or alkynyl group having up to 4 carbon atoms, which group may carry one or more halogen atoms or oxo groups or optionally substituted hydroxy, mercapto, carboxyl, carboxamido or amino groups, wherein the optional substituent is a $C_{1-4}$ alkyl, alkenyl, or alkynyl group, with the proviso that $R^3$ is other than a methyl or ethyl group; or salts thereof.

2. A compound as claimed in claim 1 in which one of $R^1$ and $R^2$ is Alk and the other is hydrogen.

3. A compound as claimed in claim 1 wherein Alk is an esterified carboxymethyl, allyl, 3-chloroallyl, propargyl or 3-chloropropargyl group.

4. A compound as claimed in claim 1 which is
1-Propargyl-5-bromopyrimid-2-one,
1-Propargyl-5-chloropyrimid-2-one,
1-(3-chloroallyl)-5-bromopyrimid-2-one,
1-Propargyl-5-fluoropyrimid-2-one,
1-(3-Chloroallyl)-5-chloropyrimid-2-one,
1-Propargyl-4-propargylthio-5-fluoropyrimid-2-one,
1-Allyl-5-chloropyrimid-2-one,
1-Allyl-5-bromopyrimid-2-one,
1-(2-Chloroethyl)-5-bromopyrimid-2-one,
1-(2-Chloroethyl)-5-chloropyrimid-2-one,
1-Propargyl-4-methylthio-5-fluoropyrimid-2-one,
Ethyl ester of 1-carboxymethyl-5-chloropyrimid-2-one,
Ethyl ester of 1-carboxymethyl-5-fluoropyrimid-2-one,
1-Allyl-5-fluoropyrimid-2-one,
1-(2-Hydroxyethyl)-5-chloropyrimid-2-one,
1-(2-Hydroxyethyl)-5-fluoropyrimid-2-one,
1-(2-Hydroxy-3-chloropropyl)-5-bromopyrimid-2-one,
1-(2-Hydroxy-3-chloropropyl)-5-chloropyrimid-2-one,
1-Propyl-5-fluoropyrimid-2-one,
1-(2-Hydroxyethyl)-5-bromopyrimid-2-one,
1-(2,3-Dihydroxypropyl)-5-chloropyrimid-2-one,
1-(2-Hydroxy-3,3,3-trichloropropyl)-5-bromopyrimid-2-one,
1-(2-Dimethylaminoethyl)-5-chloropyrimid-2-one, or
1-Carboxymethyl-5-fluoropyrimid-2-one.

5. The compound of claim 4 which is 1-propargyl-5-chloropyrimid-2-one.

6. A compound as claimed in claim 1 wherein Alk is an alkenyl or alkynyl group having up to 4 carbon atoms, which group may carry one or more halogen atoms or oxo groups or optionally substituted hydroxy, mercapto, carboxyl, carboxamido or amino groups, wherein the optional substituent is a $C_{1-4}$ alkyl, alkenyl or alkynyl group; or salts thereof.

7. A pharmaceutical composition for the inhibition of the metaphase in the growth of malignant tumors and leukaemia, comprising in association with a pharmaceutical carrier or excipient, at least one compound as claimed in claim 1.

8. A composition as claimed in claim 7 in dosage unit form, each dosage unit containing 100 mg to 1 g of said compound.

9. A composition as claimed in claim 8 also containing cytosine arabinoside.

* * * * *